United States Patent [19]

Fukuzaki et al.

[11] Patent Number: 5,034,521

[45] Date of Patent: Jul. 23, 1991

[54] PROCESS FOR PREPARING 3-SUBSTITUTED METHYL-3-CEPHEM-4-CARBOXYLIC ACID

[75] Inventors: Kentaro Fukuzaki; Wataru Takahashi, both of Nobeoka, Japan

[73] Assignee: Asahi Kasei Kogyo Kabushiki Kaisha, Osaka, Japan

[21] Appl. No.: 356,034

[22] Filed: May 22, 1989

[30] Foreign Application Priority Data

May 24, 1988 [JP] Japan .................. 63-124879

[51] Int. Cl.$^5$ ........................................ C07D 501/04
[52] U.S. Cl. .................. 540/230; 540/215; 540/221
[58] Field of Search .................. 540/230, 215

[56] References Cited

U.S. PATENT DOCUMENTS

| | | | |
|---|---|---|---|
| 3,658,799 | 4/1972 | Eardley et al. | 260/243.C |
| 3,665,003 | 5/1972 | Kennedy et al. | 260/243 C |
| 3,790,567 | 2/1974 | Kennedy et al. | 260/243 C |
| 3,846,416 | 11/1974 | Kennedy et al. | 260/243 C |
| 3,948,906 | 4/1976 | Eardley et al. | 260/243 C |
| 4,482,710 | 11/1984 | Fujimoto et al. | 364/28 |

FOREIGN PATENT DOCUMENTS 204657 12/1986 European Pat. Off. .
262744  4/1988 European Pat. Off. .
57-192392 11/1982 Japan .
59-163387  9/1984 Japan .
63-115887  5/1988 Japan .

OTHER PUBLICATIONS

Journal of Medicinal Chemistry, vol. 14, No. 2, pp. 113–116 (1971).

*Primary Examiner*—Nicholas S. Rizzo
*Attorney, Agent, or Firm*—Finnegan, Henderson, Farabow, Garrett & Dunner

[57] ABSTRACT

A novel process is disclosed for preparing a 3-substituted methyl-3-cephem-4-carboxylic acid or pharmaceutically acceptable salt thereof. The process comprises reacting a 3-acetoxymethyl-3-cephem-4-carboxylic acid or pharmaceutically acceptable salt thereof with a specific compound, such as a boric acid ester, an orthoester or an acetal, in the presence of at least one specific catalyst selected from the group consisting of Lewis acids or complexes thereof, proton acids and mixtures thereof. In the process, formation of impurities, such as a lactone, is sufficiently suppressed without protection of the carboxylic acid, so that the high purity desired product, i.e., a 3-substituted-methyl-3-cephem-4-carboxylic acid or pharmaceutically acceptable salt thereof, which is useful as an intermediate for various cephalosporin antibiotics having excellent antimicrobial activity, can be prepared in one step in high yield.

7 Claims, No Drawings

PROCESS FOR PREPARING 3-SUBSTITUTED METHYL-3-CEPHEM-4-CARBOXYLIC ACID

BACKGROUND OF THE INVENTION

1. Field Of The Invention

The present invention relates to a process for preparing 3-substituted methyl-3-cephem-4-carboxylic acids which are useful as intermediates for various cephalosporin antibiotics having a high antimicrobial activity across a broad antimicrobial spectrum. More particularly, the present invention is concerned with a process for preparing a 3-substituted methyl-3-cephem-4-carboxylic acid represented by formula (I) or a pharmaceutically acceptable salt thereof,

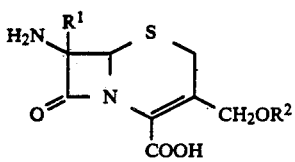

(I)

wherein $R^1$ represents a hydrogen atom or a lower alkoxy group and $R^2$ represents an unsubstituted or substituted lower alkyl group or an unsubstituted or substituted aryl group, which can be carried out in one step and which can provide the desired product with high purity in high yield.

2. Discussion Of Related Art

As a process for preparing a 3-substituted methyl-3-cephem-4-carboxylic acid represented by formula (I) from a starting 3-acetoxymethyl-3-cephem-4-carboxylic acid represented by formula (II),

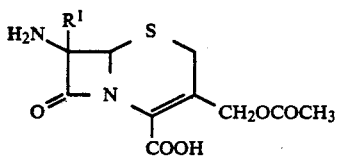

(II)

wherein $R^1$ represents a hydrogen atom or a lower alkoxy group, there have heretofore been proposed, for example, a method (1) in which the compound of formula (II) is reacted with a lower alcohol in the presence of a halide of an alkali metal, a halide of an alkaline earth metal or a halide of a quaternary ammonium (see U.S. Pat. No. 4,482,710), a method (2) in which the compound of formula (II) is reacted with a lower alcohol in the presence of boron trifluoride or a boron trifluoride complex (see European Patent Application Publication No. 204,657), a method (3) in which the compound of formula (II) is reacted a lower alcohol in the presence of an alkylsulfonic acid and a complex of boron trifluoride (see Japanese Patent Application Laid-Open Specification No. 63-115887), and a method (4) in which the compound of formula (II) is reacted with a lower alcohol in the presence of a halide of antimony, tin, iron, zinc or bismuth, or a complex thereof (see European Patent Application Publication No. 262,744).

However, none of the above-mentioned conventional methods, (1), (2), (3) and (4) can be satisfactorily practiced on a commercial scale.

According to method (1), the yield of the desired product is as low as, for example, 16 to 43%. In method (2), a lactone represented by the following formula,

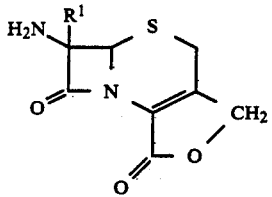

wherein $R^1$ has the same meaning as defined above, is formed as a by-product in a large amount so that there is a cumbersome problem in isolation of the desired product. That is, for isolation of the desired product from the reaction mixture containing a large amount of a lactone, (i) a large amount of a solvent for extraction-separating the lactone and/or a plurality of steps for extraction-separating the lactone are required, (ii) an extremely large amount of a resin for the separation and purification of the desired product must be used, or (iii) treatment for the precipitation-separation of the desired product at its isoelectric point must be repeated many times. Therefore, method (2) is unsatisfactory as a practical matter. Particularly, when the amount of boron trifluoride or a boron trifluoride complex is increased to improve the yield of the desired product of formula (I), formation of the undesired lactone is increased. As a result, the purity of the desired product is lowered, and isolation of the desired product becomes very cumbersome, so that loss of the desired product during the isolation is likely to be large. In methods (3) and (4), formation of the undesired lactone is not sufficiently suppressed. Accordingly, these methods are not satisfactory in yield and purity of the desired product.

Further, in other conventional processes for preparing a 3-substituted methyl-3-cephem-4-carboxylic acid, for avoiding the side reactions at the carboxyl group of the starting material, it has inevitably been necesssary to protect the carboxyl group of the starting material by, for example, esterifying the carboxyl group of the starting material prior to the reaction with the reactant. The resultant ester can be easily deesterified and, after the reaction, the esterified carboxy group is deesterified to reinstate the carboxyl group, thereby obtaining the desired product.

Therefore, there has still been a strong demand in the art for an improved practical process for preparing a 3-substituted methyl-3-cephem-4-carboxylic acid represented by formula (I), which can be carried out in one step and can provide the desired product with high purity in high yield.

SUMMARY OF THE INVENTION

The present inventors have made extensive and intensive studies with a view toward developing a novel process for preparing a 3-substituted methyl 3-cephem-4-carboxylic acid represented by formula (I) or pharmaceutically acceptable salt thereof, which can be easily practiced to give the desired product while formation of by-products, such as a lactone, is sufficiently suppressed so that the desired product with high purity is prepared in high yield on a commercial scale. As a result, it has unexpectedly been found that when 3-acetoxymethyl-3-cephem-4-carboxylic acid or pharmaceutically acceptable salt thereof is reacted with a specific compound, such as a boric acid ester, an orthoester or an acetal in the presence of a specific catalyst, the desired 3-substituted methyl-3-cephem-4-carboxylic acid or pharmaceutically acceptable salt thereof can be prepared while suppressing the formation of by-products, such as lactone, so that the desired product in high purity form can be prepared in high yield. Further, it should be noted that in this novel process employing the above-noted specific compound as a reactant, the reaction proceeds smoothly without the protection of the carboxyl group of the starting material. Therefore, the process can be carried out in one step to give the desired product with high purity in high yield. The present invention has been completed on the basis of this unexpected finding.

It is, therefore, an object of the present invention to provide a novel process for preparing a 3-substituted methyl-3-cephem-4-carboxylic acid or pharmaceutically acceptable salt thereof in high purity form, which can be practiced in one step to obtain the desired product in high yield.

The foregoing and other objects, features and advantages will be apparent to those skilled in the art from the following detailed description and the appended claims.

DETAILED DESCRIPTION OF THE INVENTION

According to the present invention, there is provided a process for preparing a 3-substituted methyl-3-cephem-4-carboxylic acid represented by formula (I) or pharmaceutically acceptable salt thereof

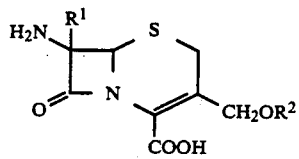

wherein $R^1$ represents a hydrogen atom or a lower alkoxy group and $R^2$ represents an unsubstituted or substituted lower alkyl group or an unsubstituted or substituted aryl group, which comprises reacting a cephalosporanic acid represented by formula (II) or pharmaceutically acceptable salt thereof

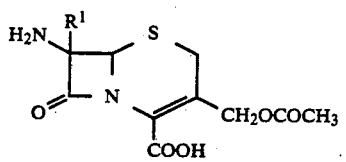

wherein $R^1$ has the same meaning as defined above, with a compound represented by formula (III)

$$Z(OR^2)_n \qquad (III)$$

wherein Z represents a boron atom or $CR^3{}_m$ wherein $R^3$ represents a hydrogen atom or a lower alkyl group and m is an integer of 1 or 2, and $R^2$ has the same meaning as defined above, and wherein when Z is a boron atom, n is 3 and when Z is $CR^3{}_m$, n is an integer of 2 or 3 with the proviso that $m+n=4$, in the presence of at least one catalyst selected from the group consisting of a proton acid, a Lewis acid and a complex of the Lewis acid.

The proton acid is selected from the group consisting of sulfuric acid, a halogenosulfuric acid, an unsubstituted or substituted arylsulfonic acid and an unsubstituted or substituted alkylsulfonic acid.

The Lewis acid is represented by formula (IV)

$$MX_l \qquad (IV)$$

wherein M represents a metal atom having a valence of 1 to 5 or a boron atom, X represents a halogen atom and l is an integer corresponding to the valence of M.

In formulae (I) and (II), $R^1$ represents a hydrogen atom or a lower alkoxy group. Representative examples of lower alkoxy groups include alkoxy groups having 1 to 4 carbon atoms, such as methoxy, ethoxy, n-propoxy, isopropoxy, n-butoxy, isobutoxy, sec-butoxy and tert-butoxy groups.

Representative examples of pharmacentically acceptable salts of the compounds represented by formulae (I) and (II) include salts at the carboxyl group and salts at the amino group. Representative examples of salts at the carboxyl group include salts with an alkali metal, such as sodium and potassium; an alkaline earth metal, such as calcium and magnesium; ammonium; a nitrogen-containing organic base, such as triethylamine, diethylamine, pyridine, N-methylpiperidine, N-methylmorpholine, N,N-dimethylaniline and dicyclohexylamine. Representative examples of salts at the amino group include salts with various acids, for example inorganic acids, such as hydrochloric acid and sulfuric acid; carboxylic acids, such as oxalic acid, formic acid, and trichloroacetic acid and trifluoroacetic acid; sulfonic acids, such as methanesulfonic acid, toluenesulfonic acid and naphthalenesulfonic acid; and Lewis acids, such as ferric chloride, antimony pentachloride and zinc chloride.

In the present invention, the compound represented by formula (III): $Z(OR^2)_n$ is a boric acid ester when Z is boron (i.e., n is 3), an orthoester when Z is $C.R^3$ (i.e., m of $CR^3{}_m$ is 1 and n is 3) wherein $R^3$ represents a hydrogen atom or a lower alkyl group, and an acetal when Z is $CR^3{}_2$, (i.e., m of $CR^3{}_2$ and n is 2) wherein $R^3$ has the same meaning as defined above. As the lower alkyl group representing $R^3$, an alkyl group having 1 to 5 carbon atoms is preferred. Representative examples of $R^2$ include lower alkyl groups having 1 to 6 carbon atoms, such as a methyl group, an ethyl group, a propyl group and a butyl group; aromatic groups, such as a phenyl group, a tolyl group and a xylyl group; and lower alkyl groups having an aromatic ring, such as a benzyl group or a phenethyl group.

In the lower alkyl groups and aromatic groups of $R^2$ and $R^3$, the hydrogen atom bonded to the carbon atom may be substituted by a halogen atom, such as fluorine, chlorine, iodine or bromine; a nitro group; an alkoxy group having 1 to 6 carbon atoms; an alkylthio group having 1 to 6 carbon atoms; an alkylamino group having 1 to 6 carbon groups; a dialkylamino group having 2 to 12 carbon atoms; an acylamino group having 1 to 6 carbon atoms; an acyl group having 1 to 6 carbon atoms or the like. Representative examples of compounds represented by formula (III) include boric acid esters, such as trimethyl borate and triethyl borate; orthoesters, such as methyl orthoformate, ethyl orthoformate, methyl orthoacetate and ethyl orthoacetate; and acetals, such as methylal, formaldehyde diethyl acetal, acetone dimethyl acetal, acetone diethyl acetal, 2,2-dimethoxybutane and 3,3-dimethoxyheptane. Of these, boric acid esters and orthoesters are particularly preferred.

The compound represented by formula (III) is generally used in a molar amount of 1 to 30 times, preferably 1 to 10 times, that of the starting cephalosporanic acid represented by formula (II) or pharmaceutically acceptable salt thereof.

In the process of the present invention, the reaction of the compound of formula (II) and the compound of formula (III) is conducted in the presence of at least one catalyst selected from the group consisting of a proton acid, a Lewis acid and a complex of said Lewis acid. The proton acid is selected from the group consisting of sulfuric acid, a halogenosulfuric acid, an unsubstituted or substituted arylsulfonic acid and an unsubstituted or substituted alkylsulfonic acid. The Lewis acid is represented by formula (IV)

$$MX_l \qquad (IV)$$

wherein M represents a metal atom having a valance of 1 to 5 or a boron atom, X represents a halogen atom and l is an integer corresponding to the valence of M.

With respect to the proton acids, more specific examples will be mentioned. Representative examples of sulfuric acids include concentrated sulfuric acid and fuming sulfuric acid. Representative examples of halogenosulfuric acids include fluorosulfuric acid and chlorosulfuric acid. Representative examples of alkylsulfonic acids include alkylsulfonic acids having 1 to 6 carbon atoms, such as methane sulfonic acid and ethanesulfonic acid. Representative examples of arylsulfonic acids include p-toluenesulfonic acid and naphthalenesulfonic acid. In the alkylsulfonic acids and arylsulfonic acids, the hydrogen atom bonded to the carbon atom may be substituted by, for example, a lower alkyl group having 1 to 6 carbon atoms; a lower alkoxy group having 1 to 6 carbon atoms; or a halogen atom, such as a fluorine atom, a chlorine atom, a bromine atom or an iodine atom.

With respect to the Lewis acids, more specific examples will be mentioned. As mentioned above, the Lewis acid is a metal halide or a halogenated boron represented by formula (IV): $MX_l$ wherein M represents a metal atom having a valence of 1 to 5 or a boron atom, X represents a halogen atom, and l is an integer corresponding to the valence of M. Representative examples of metals represented by M include antimony, iron, zinc and bismuth. Representative examples of halogen atoms include a fluorine atom, a chlorine atom, a bromine atom and an iodine atom. When M is a metal atom, X is preferably a chlorine atom, a bromine atom or an iodine atom, more preferably a chlorine atom. On the other hand, when M is a boron atom, X is preferably a fluorine atom. Representative examples of Lewis acids include halides of antimony, such as antimony pentachloride and antimony pentabromide; halides of iron, such as ferric chloride, ferric bromide and ferric iodide; halides of zinc, such as zinc chloride, zinc bromide and zinc iodide; halides of bismuth, such as bismuth chloride and bismuth bromide; and halides of boron, such as boron trifluoride.

In the process of the present invention, a complex of a Lewis acid of formula (IV) can also be used as a catalyst (hereinafter, the complex of a Lewis acid will also often be referred to simply as "Lewis acid"). The complexes of the Lewis acids include, for example complexes of metal halides, such as halides of antimony, iron, zinc and bismuth, and complexes of boron halides. Representative examples of complexes of halides of antimony, iron, zinc and bismuth include complexes thereof with dialkyl ethers, such as diethyl ether, di-n-propyl ether and di-n-butyl ether; complexes thereof with amines, such as ethylamine, n-propylamine, n-butylamine, triethanolamine and dimethylformamide; complexes thereof with fatty acids, such as acetic acid and propionic acid; complexes thereof with nitriles, such as acetonitrile and propionitrile; and complexes thereof with carboxylic acid esters, such as ethyl acetate. Representative examples of complexes of boron halides include complexes thereof with dialkyl ethers, such as diethyl ether, di-n-propyl ether and di-n-butyl ether; complexes thereof with amines, such as ethylamine, n-propylamine and n-butylamine; and complexes thereof with fatty acids, such as acetic acid and propionic acid.

The catalyst is generally used in a molar amount of 0.1 to 30 times, preferably 0.5 to 15 times, that of the starting cephalosporanic acid represented by formula (II) or pharmaceutically acceptable salt thereof.

The above-mentioned catalysts may be used individually or in combination.

In connection with the combined use of proton acids and Lewis acids, it is noted that when a proton acid is used in combination with a Lewis acid of formula (IV), proton acids other than the above-mentioned proton acids can be effectively used as the proton acids to be used in combination with the Lewis acids for exerting the desired excellent effects even though they exhibit poor catalytic effect when used alone. Representative examples of proton acids other than the above-mentioned proton acids include mineral acids, such as phosphoric acid and nitric acid; and unsubstituted or halogen-substituted acetic acids, such as trifluoroacetic acid and trichloroacetic acid. Of the proton acids to be used in combination with the Lewis acids, sulfuric acid, halogenosulfuric acids and sulfonic acid are preferred.

When a Lewis acid and a proton acid are used in combination, the total molar amount of the Lewis acid and the proton acid is generally 0.1 to 30 times, preferably 0.5 to 15 times, that of the starting cephalosporanic acid represented by formula (II) or pharmaceutically acceptable salt thereof. The equivalent ratio of the proton acid to the Lewis acid in the combined catalyst is generally 0.01 to 100, preferably 0.1 to 10. Especially when the proton acid-Lewis acid catalyst is used in a proportion such that the molar amount of the proton acid is 0.1 to 2 times that of the starting cephalosporanic acid represented by formula (II) or pharmaceutically acceptable salt thereof, an extremely excellent catalytic effect is exerted.

In the process of the present invention, when the proton acid is used as the catalyst, the reaction is accelerated and the reaction rate becomes about 5 to 10 times as fast as the rate of the reaction in which no proton acid is used, so that formation of a lactone as a by-product is suppressed, leading to a remarkable increase in the yield of the desired product represented by formula (I) or pharmaceutically acceptable salt thereof. However, when the proton acid is used in too large an amount, the effect of suppressing the formation of a lactone is relatively lowered although the reaction rate is increased. As a result, improvement in the yield of the desired product represented by formula (I) or pharmaceutically acceptable salt thereof cannot be attained. Therefore, when a proton acid is used, it is preferred to use a proton acid in combination with a Lewis acid because the combination exhibits excellent catalytic effect even if the proton acid content is small.

In the present invention, a combination of different types of Lewis acids may, of course, be used. Representative examples of combinations of Lewis acids include a combination of zinc chloride and ferric chloride, and a combination of bismuth trichloride and antimony pentachloride. The equivalent ratio of one Lewis acid to another Lewis acid is generally 0.01 to 100, preferably 0.1 to 10.

The process of the present invention is generally carried out in the presence of a solvent which does not have an adverse effect on the reaction. Representative examples of useful solvents include nitriles, such as acetonitrile, propionitrile, benzonitrile and malonitrile; nitroalkanes, such as nitromethane, nitroethane and nitropropane; aromatic hydrocarbons, such as nitrobenzene; organic carboxylic acids and esters thereof, such as acetic acid, propionic acid and trifluoroacetic acid, and esters thereof; alkyl ketones, such as acetone, methyl ethyl ketone, methyl isobutyl ketone and acetophenone; halogenated alkanes, such as dichloromethane, chloroform, dichloroethane and carbon tetrachloride; halogenated alkenes, such as dichloroethylene and trichloroethylene; acid amides, such as formamide, dimethylformamide and acetamide; ethers, such as diethyl ether, diisopropyl ether, tetrahydrofuran, dioxane and ethylene glycol dimethyl ether; aromatic hydrocarbons, such as benzene, toluene, chlorobenzene and nitrobenzene; alkanes, such as n-hexane and heptane; alicyclic compounds, such as cyclohexane; sulfolane; and dimethyl sulfoxide. The compound represented by formula (III): $Z(OR^2)_n$, which is used as a reactant may also be used as a solvent as well. Among these solvents, the compound of formula (III), an organic carboxylic acid ester, a halogenated alkane, sulfolane and mixtures thereof are preferred. The above-mentioned solvents may be used alone or in combination. These solvents may be used generally in an amount of from about 1 to about 200 times by weight, preferably from about 2 to about 30 times by weight, that of the starting material, namely the cephalosporanic acid of formula (II) or pharmaceutically acceptable salt thereof.

It is preferred that the reaction be allowed to proceed substantially in the absence of water. Accordingly, an aqueous acid solution, such as concentrated hydrochloric acid, is not suitable as a proton acid. If desired, a dehydrating agent may be added to the reaction system in order to provide reaction conditions substantially free of water. Representative examples of dehydrating agents include phosphorus compounds, such as phosphorus pentoxide, polyphosphate, phosphorus pentachloride, phosphorus trichloride and phosphorus oxychloride; organic silane derivatives, such as N,O-bis-(trimethylsilyl)acetamide, trimethylsilylacetamide, trimethylchlorosilane and dimethyldichlorosilane; acid anhydrides, such as acetic anhydride and trifluoroacetic anhydride; and inorganic desiccating agents, such as anhydrous magnesium sulfate, anhydrous calcium chloride, anhydrous calcium sulfate and Molecular Sieves. When the dehydrating agent is a phosphorus compound, an organic silane derivative or an acid anhydride, the dehydrating agent may be employed in a molar amount of from about 0.001 to about 5 times that of the starting cephalosporanic acid represented by formula (II) or pharmaceutically acceptable salt thereof. On the other hand, when the dehydrating agent is an inorganic desiccating agent, the dehydrating agent may be employed in a molar amount of from about 0.01 to about 5 times that of the starting material.

The reaction temperature is not critical. Generally, the reaction may be conducted at a temperature of from about −20° C. to about 90° C. The reaction time is also not critical and, generally, the reaction is allowed to proceed until the reaction is completed. Although the reaction time varies according to the types and amounts of the starting materials, catalysts and solvent, and the reaction temperature, the reaction time may generally be from about 1 minute to about 80 hours.

After completion of the reaction, the desired product of formula (I) or pharmaceutically acceptable salt thereof can be isolated from the reaction mixture by a conventional method. For example, cold water is added to the reaction mixture and the resulting cold mixture is then subjected to adjustment of pH to a value of from 3 to 4 to deposit the desired product as crystals. The crystals are collected. Alternatively, the reaction mixture is first subjected to adjustment of pH to a value of from 6 to 8. The formed precipitates, if any, are filtered off to obtain a filtrate. The obtained filtrate is subjected to reversed phase adsorption chromatography using a column filled with XAD-II (tradename of a resin for adsorption produced and sold by Japan Organo C.o., Ltd., Japan) or HP-20 (tradename of a resin for adsorption produced and sold by Mitsubishi C.hemical Industries, Ltd., Japan) to obtain an eluate containing the desired product. The pH value of the eluate is adjusted to a value of from 3 to 4 to deposit the desired product as crystals. The crystals are collected. Thus, a 3-substituted methyl 3-cephem-4-carboxylic acid represented by formula (I) or pharmaceutically acceptable salt thereof is obtained. In this connection, it is noted that when an iron halide, such as ferric chloride has been used as the catalyst, it is preferred that the resultant reaction mixture be treated with a reducing agent prior to the adjustment of the pH value of from about 3 to 4. This treatment with a reducing agent is effective for suppressing the decomposition of the desired product during the deposit from the pH-adjusted solution, leading to an increase in yield of the desired product. Representative examples of reducing agents include inorganic reducing agents, such as sodium thiosulfate and sodium hydrogensulfite; and organic reducing agents, such as L-ascorbic acid.

As described above, according to the process of the present invention, a 3-substituted methyl-3-cephem-4-carboxylic acid represented by formula (I) or pharmaceutically acceptable salt thereof, which is a very important intermediate for various cephalosporin antibiotics having excellent antimicrobial activity, can readily be prepared from the starting cephalosporanic acid represented by formula (II) or pharmaceutically acceptable salt thereof in high yield on a commercial scale. In the process of the present invention, it is not required to protect the carboxyl group and, therefore, a preliminary step for protecting the carboxyl group which is employed in the conventional processes can be omitted. Further, formation of a lactone as a by-product and ring cleavage or decomposition of a β-lactam ring, which are difficult problems in the conventional techniques, are remarkably suppressed. Therefore, the present invention has an advantage in that the desired product in high purity form can be prepared in one step in high yield.

DETAILED DESCRIPTION OF THE PREFERRED EMBODIMENTS

The present invention will now be described in detail with reference to the following Examples and Comparative Examples, which should not be construed to be limiting the scope of the present invention.

In the following Examples, the yield (Y) of the desired product was calculated by the following formula:

$$Y(\%) = A \div \left(B \times \frac{D}{C}\right) \times 100 \; (\%)$$

wherein A is the amount (g) of the desired product, B is the amount (g) of the starting material, C. is the molecular weight of the starting material and D is the molecular weight of the desired product.

The formation ratio of a lactone as an impurity was calculated by the above-mentioned formula except that, instead of the amount (g) of the desired product and the molecular weight of the desired prolactone the amount (g) of the lactone and the molecular weight of the lactone are respectively substituted for A and D.

Further, the content of a lactone in the desired product was shown as an index for the evaluation of the purity of the desired product.

EXAMPLE 1

To 10 ml of sulfolane were added 1.41 g of 7-aminocephalosporanic acid (hereinafter referred to as "7-ACA"), 1.96 g of ferric chloride and 1.22 ml of trimethyl borate. The mixture was heated at 30° C. for 30 hours to advance a reaction. After completion of the reaction, the reaction mixture was cooled to −10° C. To the reaction mixture were added 30 ml of water and 10 ml of methanol. Then, the mixture was adjusted to pH 7.8 with aqueous ammonia at a temperature of from −2° C. to 2° C. The resultant precipitate was filtered off, and then washed with water. The filtrate was combined with the washings. The resultant mixture was adjusted to pH 3.5, which was the isoelectric point of the desired product, with 36% hydrochloric acid to thereby form a precipitate. The precipitate was collected by filtration to separate the precipitate from a lactone as an impurity, and washed with 10 ml of cold water and, then, with 20 ml of cold methanol, to thereby obtain the desired product, namely 7-amino-3-methoxy -methyl-3-cephem-4-carboxylic acid. The amount of the desired product was 0.70 g. The yield of the desired product was 55%.

It was also found that as a by-product, 0.075 g of a lactone was formed (formation ratio: 6.0%). The content of the lactone in the 7-amino-3-metho xymethyl-3-cephem-4-carboxylic acid was 0.22%.

The molecular structure of the desired product was analyzed by nuclear magnetic resonance (hereinafter referred to as "NMR") and infrared (hereinafter referred to as "IR") spectrophotometry. The results are as follows.

NMR (solvent: CF₃COOD)
Chemical shift [ppm]
3.63 (3H, s, —CH₂OCH₃)
3.77 (2H, s, —CH₂— at the 2-position)
4.86 (2H, s, —CH₂OCH₃)
5.43 (2H, s, H at the 6—and 7-positions)
IR spectrum (Nujol method)
(cm⁻¹)
3160 (—NH₂)
1800 (>C=O, β-lactam)
1620 (—COOH)
1100 (—CH₂OCH₃)

EXAMPLE 2

To 10 ml of dichloromethane were added 1.41 g of 7-ACA, 2.18 g of concentrated sulfuric acid and 1.88 ml of trimethyl borate. The reaction was conducted at 0° C. for one hour. After completion of the reaction, substantially the same procedure as in Example 1 was repeated, to thereby obtain the desired product, namely 7-amino-3-methoxymethyl-3-cephem-4-carboxylic acid. The amount of the desired product was 0.63 g. The yield of the desired product was 50%.

It was also found that as a by-product, 0.07 g of a lactone was formed (formation ratio: 6.3%). The content of the lactone in the 7-amino-3-methoxy methyl-3-cephem-4-carboxylic acid was 0.22%.

The molecular structure of the desired product was analyzed by NMR and IR spectrophotometry. The results were the same as those obtained in Example 1.

EXAMPLE 3

To 10 ml of dichloromethane were added 1.41 g of 7-ACA, 5.1 ml of methanesulfonic acid and 1.07 ml of trimethyl borate. The reaction was conducted at 0° C. for 9 hours. After completion of the reaction, substantially the same procedure as in Example 1 was repeated, to thereby obtain the desired product, namely 7-amino-3-methoxymethyl-3-cephem-4-carboxylic acid. The amount of the desired product was 0.70 g. The yield of the desired product was 55%.

It was also found that as a by-product, 0.07 g of a lactone was formed (formation ratio: 6.3%). The content of the lactone in the 7-amino-3-methoxy- methyl-3-cephem-4-carboxylic acid was 0.22%.

The molecular structure of the desired product was analyzed by NMR and IR spectrophotometry. The results were the same as those obtained in Example 1.

EXAMPLE 4

To 10 ml of sulfolane were added 1.41 g of 7-ACA, 1.96 g of ferric chloride, 0.29 ml of concentrated sulfuric acid and 1.22 ml of trimethyl borate. The mixture was heated at 30° C. for 3 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 1.00 g. The yield of the desired product was 79%.

It was also found that as a by-product, 0.073 g of a lactone was formed (formation ratio: 6.6%). The content of the lactone in the 7-amino-3-methoxy- methyl-3-cephem-4-carboxylic acid was 0.24%.

The molecular structure of the desired product was analyzed by NMR and IR spectrophotometry. The results were the same as those obtained in Example 1.

EXAMPLE 5

To 20 ml of sulfolane were added 1.41 g of 7-ACA, 1.96 g of ferric chloride, 0.29 ml of concentrated sulfuric acid and 1.22 ml of trimethyl borate. The mixture was heated at 30° C. for 3 hours to advance a reaction. After completion of the reaction, the reaction mixture was cooled to 0° C. To the reaction mixture were added 30 ml of water, 10 ml of methanol and 3.04 g of sodium thiosulfate and the mixture was stirred for 1 hour while cooling with ice. The resultant precipitate was filtered off, and then washed with methanol. The filtrate was combined with the washings. The resultant mixture was adjusted to pH 3.5 with 36% hydrochloric acid to thereby form a precipitate. The precipitate was collected by filtration, and washed with 10 ml of cold water and, then, with 20 ml of cold methanol, to thereby obtain the desired product, namely 7-amino-3-methoxymethyl-3-cephem-4-carboxylic acid. The amount of the desired product was 1.05 g. The yield of the desired product was 83%.

It was also found that as a by-product, 0.073 g of a lactone was formed (formation ratio: 6.6%). The content of the lactone in the 7-amino-3-methoxy- methyl-3-cephem-4-carboxylic acid was 0.24%.

The molecular structure of the desired product was analyzed by NMR and IR spectrophotometry. The results were the same as those obtained in Example 1.

EXAMPLE 6

To 20 ml of sulfolane were added 1.41 g of 7-ACA, 3.2 ml of boron trifluoride ethyl ether, 0.84 ml of concentrated sulfuric acid and 6.12 ml of trimethyl borate. The mixture was heated at 30° C. for 4 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.86 g. The yield of the desired product was 68%.

It was also found that as a by-product, 0.080 g of a lactone was formed (formation ratio: 7.2%). The content of the lactone in the 7-amino-3-methoxy- methyl-3-cephem-4-carboxylic acid was 0.26%.

The molecular structure of the desired product was analyzed by NMR and IR spectrophotometry. The results were the same as those obtained in Example 1.

EXAMPLE 7

To 10 ml of methyl acetate were added 1.41 g of 7-ACA, 3.0 g of zinc chloride, 0.29 ml of concentrated sulfuric acid and 3.13 ml of trimethyl borate. The mixture was heated at 30° C. for 6 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.86 g. The yield of the desired product was 69%.

It was also found that as a by-product, 0.049 g of a lactone was formed (formation ratio: 4.5%). The content of the lactone in the 7-amino-3-methoxy- methyl-3-cephem-4-carboxylic acid was 0.17%.

The molecular structure of the desired product was analyzed by NMR and IR spectrophotometry. The results were the same as those obtained in Example 1.

EXAMPLE 8

To 10 ml of sulfolane were added 1.41 g of 7- ACA, 1.2 ml of antimony pentachloride, 0.58 ml of concentrated sulfuric acid and 1.95 ml of trimethyl borate. The reaction was conducted at 0° C. for 7 hours. After completion of the reaction, substantially the same procedure as in Example 1 was repeated to thereby obtain the desired product, namely, 7-amino-3-methoxymethyl-3-cephem-4-carboxylic acid. The amount of the desired product was 1.04 g. The yield of the desired product was 82%.

It was also found that as a by-product, 0.064 g of a lactone was formed (formation ratio: 5.8%). The content of the lactone in the 7-amino-3-methoxy -methyl-3-cephem-4-carboxylic acid was 0.15%.

The molecular structure of the desired product was analyzed by NMR and IR spectrophotometry. The results were the same as those obtained in Example 1.

EXAMPLE 9

To 10 ml of sulfolane were added 1.41 g of 7-ACA, 1.96 g of ferric chloride, 0.35 ml of methanesulfonic acid and 1.95 ml of trimethyl borate. The mixture was heated at 30° C. for 5 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.74 g. The yield of the desired product was 58%.

It was also found that as a by-product, 0.037 g of a lactone was formed (formation ratio: 3.4%). The content of the lactone in the 7-amino-3-methoxy methyl-3-cephem-4-carboxylic acid was 0.20%.

The molecular structure of the desired product was analyzed by NMR and IR spectrophotometry. The results were the same as those obtained in Example 1.

EXAMPLE 10

To 10 ml of sulfolane were added 1.41 g of 7-ACA, 1.96 g of ferric chloride, 0.40 ml of trifluoroacetic acid and 1.95 ml of trimethyl borate. The mixture was heated at 30° C. for 5 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.70 g. The yield of the desired product was 55%.

It was also found that as a by-product, 0.027 g of a lactone was formed (formation ratio: 2.5%). The content of the lactone in the 7-amino-3-methoxy methyl-3-cephem-4-carboxylic acid was 0.10%.

The molecular structure of the desired product was analyzed by NMR and IR spectrophotometry. The results were the same as those obtained in Example 1.

EXAMPLE 11

To 10 ml of sulfolane were added 1.41 g of 7-ACA, 0.93 g of ferric chloride, 5.25 g of zinc chloride and 3.13 ml of trimethyl borate. The mixture was heated at 50° C. for 5 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.89 g. The yield of the desired product was 70%.

It was also found that as a by-product, 0.089 g of a lactone was formed (formation ratio: 8.1%). The content of the lactone in the 7-amino-3-methoxy methyl-3-cephem-4-carboxylic acid was 0.28%.

The molecular structure of the desired product was analyzed by NMR and IR spectrophotometry. The results were the same as those obtained in Example 1.

EXAMPLE 12

To 10 ml of sulfolane were added 1.41 g of 7-ACA, 0.60 ml of antimony pentachloride, 15.18 g of bismuth trichloride and 1.95 ml of trimethyl borate. The mixture was heated at 50° C. for 5 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.81 g. The yield of the desired product was 64%.

It was also found that as a by-product, 0.098 g of a lactone was formed (formation ratio: 8.9%). The content of the lactone in the 7-amino-3-methoxy methyl-3-cephem-4-carboxylic acid was 0.29%.

The molecular structure of the desired product was analyzed by NMR and IR spectrophotometry. The results were the same as those obtained in Example 1.

EXAMPLE 13

To 10 ml of sulfolane were added 1.41 g of 7-ACA, 6.0 g of zinc chloride, 0.34 ml of methanesulfonic acid and 3.06 ml of trimethyl borate. The mixture was heated at 30° C. for 23 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.95 g. The yield of the desired product was 75%.

It was also found that as a by-product, 0.044 g of a lactone was formed (formation ratio: 4.0%). The content of the lactone in the 7-amino-3-methoxy methyl-3-cephem-4-carboxylic acid was 0.17%.

The molecular structure of the desired product was analyzed by NMR and IR spectrophotometry. The results were the same as those obtained in Example 1.

EXMAPLE 14

To 10 ml of sulfolane were added 1.41 g of 7-ACA, 2.4 ml of boron trifluoride ethyl ether, 0.34 ml of methanesulfonic acid and 3.13 ml of trimethyl borate. The mixture was heated at 30° C. for 5 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.49 g. The yield of the desired product was 39%.

It was also found that as a by-product, 0.055 g of a lactone was formed (formation ratio: 5.0%). The content of the lactone in the 7-amino-3-methoxy methyl-3-cephem-4-carboxylic acid was 0.27%.

The molecular structure of the desired product was analyzed by NMR and IR spectrophotometry. The results were the same as those obtained in Example 1.

EXAMPLE 15

To 20 ml of sulfolane were added 1.41 g of 7-ACA, 8.2 ml of boron trifluoride ethyl ether, 1.9 ml of fluorosulfonic acid and 6.12 ml of trimethyl borate. The mixture was heated at 25° C. for 20 minutes to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.76 g. The yield of the desired product was 60%.

It was also found that as a by-product, 0.082 g of a lactone was formed (formation ratio: 7.5%). The content of the lactone in the 7-amino-3-methoxy methyl-3-cephem-4-carboxylic acid was 0.30%.

The molecular structure of the desired product was analyzed by NMR and IR spectrophotometry. The results were the same as those obtained in Example 1.

COMPARATIVE EXAMPLE 1

To 10 ml of sulfolane were added 1.41 g of 7-ACA, 5.8 ml of boron trifluoride ethyl ether and 0.84 ml of methanol. The mixture was heated at 50° C. for 1.25 hours to advance a reaction. After completion of the reaction, substantially the same procedure dure as in Example 1 was repeated, to thereby obtain the desired product, namely 7-amino-3-methoxy methyl-3-cephem-4-carboxylic acid. The amount of the desired product was 0.23 g. The yield of the desired product was 18%.

It was also found that as a by-product, 0.23 g of a lactone was formed (formation ratio: 21%). The content of the lactone in the 7-amino-3-methoxy methyl-3-cephem-4-carboxylic acid was 1.9%.

COMPARATIVE EXAMPLE 2

To 10 ml of sulfolane were added 1.41 g of 7-ACA, 6.3 ml of boron trifluoride ethyl ether and 2.30 ml of methanol. The mixture was heated at 50° C. for 3.5 hours to advance a reaction. After completion of the reaction, substantially the same procedure as in Example 1 was repeated, to thereby obtain the desired product, namely 7-amino-3-methoxy methyl-3-cephem-4-carboxylic acid. The amount of the desired product was 0.87 g. The yield of the desired product was 69%.

It was also found that as a by-product, 0.13 g of a lactone was formed (formation ratio: 12%). The content of the lactone in the 7-amino-3-methoxy methyl-3-cephem-4-carboxylic acid was 1.1%.

COMPARTATIVE EXAMPLE 3

To 10 ml of dichloromethane were added 1.41 g of 7-ACA, 5.1 ml of methanesulfonic acid and 1.23 ml of methanol. The reaction was conducted at 0° C. for 6 hours. After completion of the reaction, the reaction mixture was poured into ice water. Then, the resultant mixture was adjusted to pH 3.5 with 10% aqueous sodium hydroxide to form a precipitate. The precipitate was collected by filtration, and then washed with water and dried to obtain the desired product, namely 7-amino-3-methoxymethyl-3-cephem-4-carboxylic acid. The amount of the desired product was 1.14 g. The yield of the desired product was 65%.

It was also found that as a by-product, 0.25 g of a lactone was formed (formation ratio: 22%). The content of the lactone in the 7-amino-3-methoxy- methyl-3-cephem-4-carboxylic acid was 1.8%.

COMPARATIVE EXAMPLE 4

To 10 ml of dichloromethane were added 1.41 g of 7-ACA, 2.1 ml of concentrated sulfuric acid and 1.05 ml of methanol. The reaction was conducted at 0° C. for 1.75 hours. After completion of the reaction, substantially the same procedure as in Example 1 was repeated, to thereby obtain the desired product, namely 7-amino-3-methoxymethyl-3-cephem-4-carboxylic acid. The amount of the desired product was 0.27 g. The yield of the desired product was 21%.

It was also found that as a by-product, 0.37 g of a lactone was formed (formation ratio: 34%). The content of the lactone in the 7-amino-3-methoxy methyl-3-cephem-4-carboxylic acid was 2.5%.

COMPARATIVE EXAMPLE 5

To 10 ml of sulfolane were added 1.41 g of 7-ACA, 1.96 g of ferric chloride, 0.29 ml of concentrated sulfuric acid and 0.45 ml of methanol. The mixture was heated at 30° C. for 2 hours to advance a reaction. After completion of the reaction, substantially the same procedure as in Example 1 was repeated, to thereby obtain the desired product, namely 7-amino-3-methoxymethyl-3-cephem-4-carboxylic acid. The amount of the desired product was 0.71 g. The yield of the desired product was 56%.

It was also found that as a by-product, 0.35 g of a lactone was formed (formation ratio: 32%). The content of the lactone in the 7-amino-3-methoxy methyl-3-cephem-4-carboxylic acid was 2.8%.

EXAMPLE 16

To 10 ml of sulfolane were added 1.41 g of 7-ACA, 0.99 g of ferric chloride, 5.00 g of zinc chloride and 0.92 ml of methyl orthoformate. The mixture was heated at 50° C. for 6 hours to advance a reaction. After completion of the reaction, substantially the same procedure as in Example 1 was repeated, to thereby obtain a desired product, namely 7-amino-3-methoxymethyl-3-cephem-4-carboxylic acid. The amount of the desired product was 0.81 g. The yield of the desired product was 64%.

It was also found that as a by-product, 0.10 g of a lactone was formed (formation ratio: 9.2%). The content of the lactone in the 7-amino-3-methoxy- methyl-3-cephem-4-carboxylic acid was 0.84%.

The molecular structure of the desired product was analyzed by NMR and IR spectrophotometry. The results were the same as those obtained in Example 1.

EXAMPLE 17

To 10 ml of sulfolane were added 1.41 g of 7-ACA, 0.3 ml of concentrated sulfuric acid, 1.96 g of ferric chloride and 1.15 ml of methyl orthoformate. The mixture was heated at 30° C. for 5 hours to advance a reaction. After completion of the reaction, substantially the same procedure as in Example 1 was repeated, to thereby obtain a desired product, namely 7-amino-3-methoxymethyl-3-cephem-4-carboxylic acid. The amount of the desired product was 0.75 g. The yield of the desired product was 59%.

It was also found that as a by-product, 0.12 g of a lactone was formed (formation ratio: 10.9%). The content of the lactone in the 7-amino-3-methoxy methyl-3-cephem-4-carboxylic acid was 1.0%.

The molecular structure of the desired product was analyzed by NMR and IR spectrophotometry. The results were the same as those obtained in Example 1.

COMPARATIVE EXAMPLE 6

In 3 ml of nitromethane were dispersed 1.44 g of 7-ACA and 1.19 g of methanol. Then, to the dispersion were sequentially added 8.54 g of a complex of boron trifluoride with methanol (content of boron trifluoride: 51%) and 3.31 g of fluorosulforic acid. The resultant mixture was heated at 25° C. for 15 min while stirring to advance a reaction. After completion of the reaction, the reaction mixture was cooled to 0° C. Then, from the reaction mixture, methanol was distilled off under reduced pressure. To the resultant residue was added 100 ml of water to obtain a solution. The solution was subjected to reversed phase adsorption chromatography using a column filled with HP-20 (tradename of a resin for adsorption produced and sold by Mitsubishi Chemical Industries, Ltd., Japan). The eluate was adjusted to pH 3.5 with 28% aqueous ammonia to thereby form a precipitate. The precipitate was collected by filtration, and washed with 15 ml of ice water and, then, with 5 ml of cold methanol to thereby obtain the desired product, namely 7-amino-3-methoxy methyl-3-cephem-4-carboxylic acid. The amount of the desired product was 0.75 g. The yield of the desired product was 55.8%.

It was also found that as a by-product, 0.24 g of a lactone was formed (formation ratio: 21%). The content of the lactone in the 7-amino-3-methoxy methyl-3-cephem-4-carboxylic acid was 2.8%.

COMPARATIVE EXAMPLE 7

In 10 ml of nitromethane were dispersed 2.72 g of 7-ACA, 9.63 g of zinc chloride and 0.71 g of methanol. The dispersion was heated at 60° C. for 90 minutes to advance a reaction. After completion of the reaction, the reaction mixture was cooled to about 5° C. To the reaction mixture were added 30 ml of water and 10 ml of methanol. Then, the mixture was adjusted to pH 7.8 with 28% aqueous ammonia at a of from −2° C. to 2° C. The resultant precipitate was filtered off, and then washed with water. The filtrate was combined with the washings. The resultant mixture was adjusted to pH 3.5 with 36% hydrochloric acid to thereby form a precipitate. The precipitate was collected by filtration, and washed with 10 ml of cold water and, then, with 20 ml of cold methanol, to thereby obtain the desired product, namely 7-amino-3-methoxymethyl-3-cephem-4-carboxylic acid. The amount of the desired product was 0.98 g. The yield of the desired product was 40%.

It was also found that as a by-product, 0.38 g of a lactone was formed (formation ratio: 18%). The content of the lactone in the 7-amino-3-methoxy- methyl-3-cephem-4-carboxylic acid was 2.4%.

What is claimed is:

1. A process for preparing a 3-substituted methyl-3-cephem-4-carboxylic acid represented by formula (I) or a pharmaceutically acceptable salt thereof

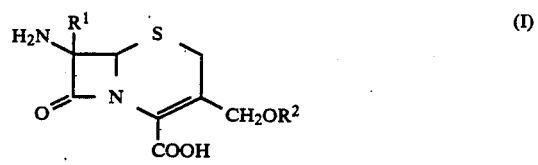

wherein $R^1$ represents a hydrogen atom or a lower alkoxy group and $R^2$ represents a lower alkyl group unsubstituted or substituted with a halogen atom; a nitro group; an alkoxy group having 1 to 6 carbon atoms; an alkylthio group having 1 to 6 carbon atoms; an alkylamino group having 1 to 6 carbon atoms; a dialkylamino group having 2 to 12 carbon atoms; an acylamino group having 1 to 6 carbon atoms; or an acyl group having 1 to 6 carbon atoms, or an aryl group selected from the group consisting of a phenyl group, a tolyl group, a xylyl group, a benzyl group and a phenethyl group, said aryl group being unsubstituted or substituted wth a halogen atom; a nitro group; an alkoxy group having 1 to 6 carbon atoms; an alkylthio group having 1 to 6 carbon atoms; an alkylamino group having 1 to 6 carbon atoms; a dialkylamino group having 2 to 12 carbon atoms; an acylamino group having 1 to 6 carbon atoms;

or an acyl group having 1 to 6 carbon atoms, which comprises reacting a cephalosporanic acid represented by formula (II) or a pharmaceutically acceptable salt thereof

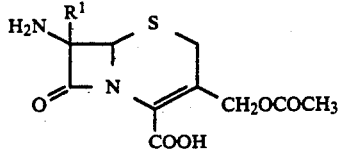

(II)

wherein $R^1$ has the same meaning as defined above, with a compound represented by formula (III)

$$Z(OR^2)_n \qquad \text{(III)}$$

wherein Z represents a boron atom or $CR^3{}_m$ wherein $R^3$ represents a hydrogen atom or a lower alkyl group and m is an interger of 1 or 2, and $R^2$ has the same meaning as defined above, and wherein when Z is a boron atom, n is 3 and when Z is $CR^3{}_m$, n is an integer of 2 or 3 with the proviso that $m+n=4$, in the presence of at least one catalyst selected from the group consisting of a proton acid, a Lewis acid and a complex of said Lewis acid, said proton acid being selected from the group consisting of sulfuric acid, a halogenosulfuric acid, a p-toluenesulfonic acid unsubstituted or substituted with a lower alkyl group having 1 to 6 carbon atoms; a lower alkoxy group having 1 to 6 carbon atoms; or a halogen atom, naphthalenesulfonic acid unsubstituted or substituted with a lower alkyl group having 1 to 6 carbon atoms; a lower alkoxy group having 1 to 6 carbon atoms; or a halogen atom, and an alkylsulfonic acid unsubstituted or substituted with a lower alkyl group having 1 to 6 carbon atoms; a lower alkoxy group having 1 to 6 carbon atoms; or a halogen atom, said Lewis acid being represented by formula (IV)

$$MX_l \qquad \text{(IV)}$$

wherein M represents a metal atom having a valance of 1 to 5 or a boron atom, X represents a halogen atom, and l is an integer corresponding to the valance of M.

2. The process according to claim 1, wherein said compound represented by formula (III) is a boric acid ester represented by $B(OR^2)_3$ or an orthoformic ester represented by $CH(OR^2)_3$.

3. The process according to claim 2, wherein $R^2$ is a methyl group.

4. The process according to claim 1, wherein said catalyst is used in a molar amount of 0.1 to 30 times that of said cephalosporanic acid or pharmaceutically acceptable salt thereof.

5. The process according to claim 1, wherein said catalyst comprises a combination of said proton acid with said Lewis acid or with said complex of Lewis acid.

6. The process according to claim 5, wherein the equivalent ratio of said proton acid to said Lewis acid or to said complex of Lewis acid in said combination is 0.1 to 10.

7. The process according to claim 1, wherein the reaction is conducted in a solvent selected from the group consisting of said compound of formula (III), an organic carboxylic acid ester, a halogenated alkane, sulfolane and mixtures thereof.

* * * * *